United States Patent
Lee

(10) Patent No.: US 10,111,736 B2
(45) Date of Patent: Oct. 30, 2018

(54) HERMETIC TOOTH CLEANING DEVICE

(71) Applicant: Bluereo Inc., Seoul (KR)

(72) Inventor: Seung Min Lee, Seoul (KR)

(73) Assignee: Bluereo Inc., Seoul (KR)

( * ) Notice: Subject to any disclaimer, the term of this patent is extended or adjusted under 35 U.S.C. 154(b) by 0 days.

(21) Appl. No.: 15/506,188

(22) PCT Filed: Jun. 2, 2016

(86) PCT No.: PCT/KR2016/005829
§ 371 (c)(1),
(2) Date: Feb. 23, 2017

(87) PCT Pub. No.: WO2017/119554
PCT Pub. Date: Jul. 13, 2017

(65) Prior Publication Data
US 2018/0028296 A1    Feb. 1, 2018

(30) Foreign Application Priority Data

Jan. 8, 2016  (KR) .......................... 10-2016-0002648

(51) Int. Cl.
*A61C 17/028*    (2006.01)
*A61C 17/22*    (2006.01)
(Continued)

(52) U.S. Cl.
CPC ............ *A61C 17/222* (2013.01); *A46B 11/00* (2013.01); *A46B 11/06* (2013.01); *A61C 17/028* (2013.01);
(Continued)

(58) Field of Classification Search
CPC ... A61C 17/222; A61C 17/227; A61C 17/028; A61C 17/221; A61C 17/3481;
(Continued)

(56) References Cited

U.S. PATENT DOCUMENTS 6,689,078 B1 *   2/2004   Rehkemper ............ A61C 17/30
                                                           15/29
7,004,662 B1 *   2/2006   Gordon .............. A46B 11/0017
                                                           401/180
(Continued)

FOREIGN PATENT DOCUMENTS

| JP | 2000-225023 A | 8/2000 |
| JP | 5505414 B2 | 5/2014 |
| KR | 10-1981-0001342 B1 | 10/1981 |
| KR | 10-2012-0088255 A | 8/2012 |
| KR | 10-1541176 B1 | 8/2015 |
| KR | 10-1571095 B1 | 11/2015 |

OTHER PUBLICATIONS

English Translation for Written Opinion of the ISA dated Aug. 9, 2016.*

*Primary Examiner* — Quang D Thanh
(74) *Attorney, Agent, or Firm* — Novick, Kim & Lee, PLLC; Sang Ho Lee

(57) ABSTRACT

The present disclosure relates to a hermetic tooth cleaning device, and more particularly, to a hermetic tooth cleaning device including: a main body which includes an outer case; a cleaning body which is coupled to the main body, and has an internal fluid conduit formed therein such that at least one nozzle is formed to be opened at one end of the internal fluid conduit, and an accommodating portion is formed at the other end of the internal fluid conduit; a connecting unit which couples the main body and the cleaning body, and has a connecting flow path formed therein, one side fixedly coupled to the main body, and the other side inserted into the accommodating portion; and a first sealing unit which is provided between the cleaning body and the connecting unit, and has a hollow space formed therein, thereby preventing a loss of positive pressure or negative pressure and a leak of gargling water or a cleaning solution by improving sealing performance of a flow path that connects a drive unit and the nozzle.

10 Claims, 12 Drawing Sheets

(51) Int. Cl.
  *A46B 11/00* (2006.01)
  *A46B 11/06* (2006.01)
  *A61C 17/02* (2006.01)
  *A61C 17/28* (2006.01)
  *A61C 17/34* (2006.01)
(52) U.S. Cl.
  CPC ........ *A61C 17/0208* (2013.01); *A61C 17/227* (2013.01); *A61C 17/28* (2013.01); *A61C 17/3481* (2013.01); *A46B 2200/1066* (2013.01); *A61C 17/221* (2013.01)
(58) Field of Classification Search
  CPC ..... A61C 17/28; A61C 17/0208; A46B 11/00; A46B 2200/1066; A46B 11/06
  See application file for complete search history.

(56) References Cited

U.S. PATENT DOCUMENTS

| | | | | |
|---|---|---|---|---|
| 2007/0041779 | A1* | 2/2007 | Kuo | A46B 11/0058 401/188 R |
| 2009/0136285 | A1* | 5/2009 | Hall | A61C 17/222 401/282 |
| 2012/0077145 | A1* | 3/2012 | Tsurukawa | A46B 5/0095 433/82 |
| 2015/0282908 | A1* | 10/2015 | Wada | A61C 17/0202 433/89 |
| 2017/0042638 | A1* | 2/2017 | Lee | A61C 17/028 |

\* cited by examiner

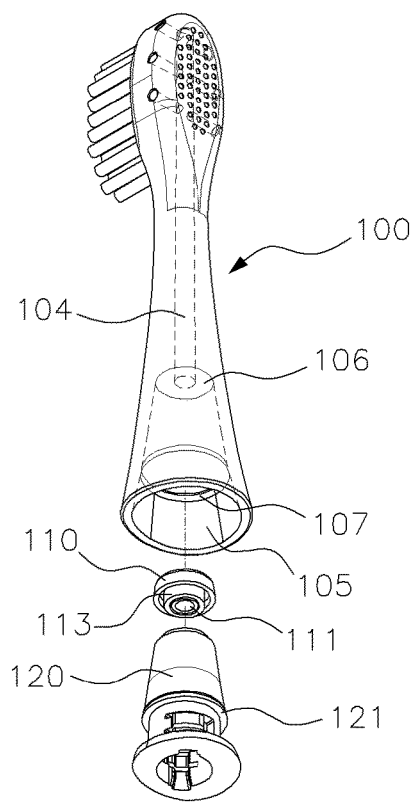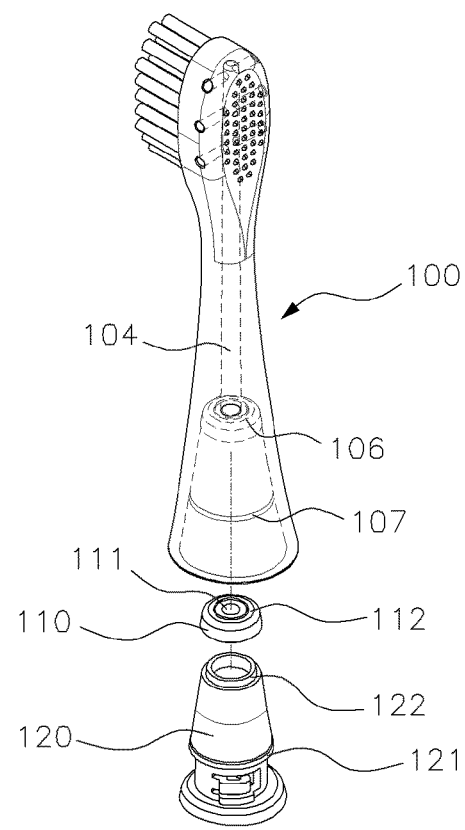
FIG. 6A  FIG. 6B
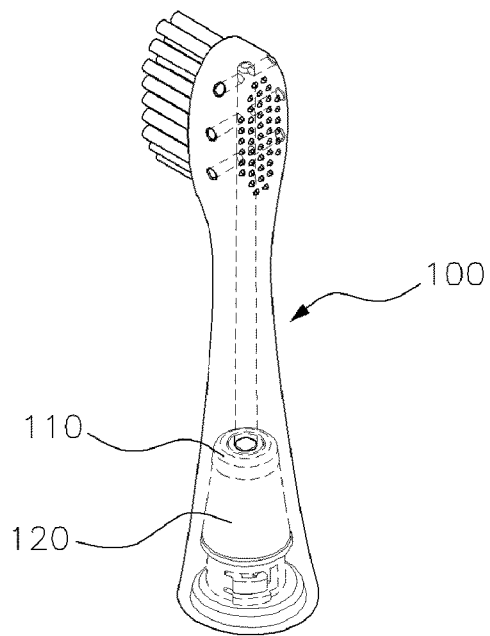
FIG. 6C

HERMETIC TOOTH CLEANING DEVICE

This application is prepared under the Research and Business Development program, which is funded by the Ministry of Trade, Industry and Energy (N002012), Republic of Korea.

TECHNICAL FIELD

The present disclosure relates to a tooth cleaning device, and more particularly, to a tooth cleaning device capable of supplying a cleaning solution or discharging a fluid in the mouth to the outside through a flow path formed in the tooth cleaning device.

BACKGROUND ART

The most typical tool for cleaning teeth is a toothbrush, and the toothbrush is a tool used to clean the teeth with toothpaste attached to the toothbrush for the purpose of health care, hygiene, and cleanliness for the teeth. The toothbrush includes a handle portion formed in the form of a stick, and a brush formed by densely planting thin bristle members on a body formed at a tip of the handle portion.

Further, when cleaning the teeth, a user attaches the brush of the toothbrush onto the teeth and repeatedly performs an operation of removing gargling water in the mouth while rubbing the teeth, and after brushing the teeth, the user washes the interior of the mouth with cleaning water, and then spits out the gargling water.

A traditional toothbrush in the related art is used only to clean the teeth, but recently, researches are being conducted on a multifunctional tooth cleaning device capable of supplying a cleaning solution or suctioning gargling water through a nozzle formed in the toothbrush.

In general, to supply the cleaning solution or suction the gargling water, a separate drive unit, which may provide positive pressure or negative pressure, is required, and the drive unit may be mounted inside or outside the tooth cleaning device.

The drive unit is connected with the nozzle formed in the toothbrush through a flow path, and the cleaning solution to be supplied to the interior of the mouth or the gargling water to be suctioned from the interior of the mouth may flow through the flow path by the positive pressure or the negative pressure provided by the drive unit.

Meanwhile, in a case in which the tooth cleaning device has a structure in which one or more sections from the nozzle to the drive unit may be separated, the flow path also needs to have a structure formed by coupling a plurality of sub flow paths such as connecting tubes or internal fluid conduits which are separable.

In this case, connecting units are present between the sub flow paths, and because of the connecting units, there are problems in that the pressure provided by the drive unit is not appropriately transmitted to the nozzle, the pressure is partially lost, and the gargling water or the cleaning solution leaks.

As literature in the related art, there is Korean Patent Application Laid-Open No. 10-2012-0088255 (entitled "Toothbrush with Suctioning Function", published on Aug. 8, 2012).

DISCLOSURE

Technical Problem

An object of the present disclosure for solving the aforementioned problems is to provide a hermetic tooth cleaning device capable of preventing a loss of positive pressure or negative pressure and a leak of gargling water or a cleaning solution by improving sealing performance of a flow path that connects a drive unit and a nozzle.

Technical Solution

To achieve the above object, a hermetic tooth cleaning device according to an exemplary embodiment of the present disclosure includes: a main body which includes an outer case; a cleaning body which is coupled to the main body, and has an internal fluid conduit formed therein such that at least one nozzle is formed to be opened at one end of the internal fluid conduit, and an accommodating portion is formed at the other end of the internal fluid conduit; a connecting unit which couples the main body and the cleaning body, and has a connecting flow path formed therein, one side fixedly coupled to the main body, and the other side inserted into the accommodating portion; and a first sealing unit which is provided between the cleaning body and the connecting unit, and has a hollow space formed therein.

In addition, according to the exemplary embodiment of the present disclosure, a flange is separably coupled to an outer portion of the connecting unit, and the flange is inserted and fixed into the accommodating portion.

In addition, according to the exemplary embodiment of the present disclosure, a protruding portion and a depressed portion, which correspond to each other, are formed at the flange and the first sealing unit, respectively, and the protruding portion is inserted into the depressed portion.

In addition, according to the exemplary embodiment of the present disclosure, the internal fluid conduit, the hollow space, and the connecting flow path are connected to form a continuous flow path.

In addition, according to the exemplary embodiment of the present disclosure, a first catching projection is formed on an inner surface of the accommodating portion, a catching protrusion is formed on an outer surface of the flange, and the catching protrusion is caught and fixed by the first catching projection when the flange is inserted into the accommodating portion.

In addition, according to the exemplary embodiment of the present disclosure, a second sealing unit is provided between the outer case and the connecting unit, and the connecting unit is penetratively coupled to the second sealing unit.

In addition, according to the exemplary embodiment of the present disclosure, the connecting unit has an insertion portion which protrudes to a predetermined height so as to be inserted into the accommodating portion.

In addition, according to the exemplary embodiment of the present disclosure, a first fastening protruding portion and a fastening guide portion, which correspond to each other, are formed at the insertion portion and the second sealing unit, respectively, such that during a process in which the insertion portion is penetratively coupled to the second sealing unit, the first fastening protruding portion is guided along the fastening guide portion and then caught and fixed by an end of the fastening guide portion.

In addition, according to the exemplary embodiment of the present disclosure, a coupling protruding portion, which protrudes inward, is formed at one end of the outer case, and a coupling recess, which corresponds to the coupling protruding portion, is formed at an upper end of the second sealing unit, such that during a process in which the connecting unit is coupled to the outer case, the coupling protruding portion is seated on the coupling recess.

In addition, according to the exemplary embodiment of the present disclosure, a second fastening protruding portion and a coupling channel, which correspond to each other, are formed at the insertion portion and the flange, respectively, such that during a process in which the insertion portion is coupled to the flange, the second fastening protruding portion is guided along the coupling channel and then caught and fixed by one side of the coupling channel.

In addition, according to the exemplary embodiment of the present disclosure, the coupling channel includes an introduction portion which is opened outward at one end thereof, and an extension guide portion which extends from the introduction portion in a direction in which the flange and the connecting unit are coupled to each other.

In addition, according to the exemplary embodiment of the present disclosure, a second catching projection is formed at one side of the extension guide portion, and the second fastening protruding portion, which is guided to the extension guide portion, is seated on a seating portion after passing over the second catching projection.

Advantageous Effects

According to the present disclosure, it is possible to prevent a loss of positive pressure or negative pressure generated by the drive unit and thus to improve performance of the tooth cleaning device by improving sealing performance of the flow path that connects the drive unit and the nozzle, and it is possible to improve durability of the tooth cleaning device by preventing a leak of the cleaning solution to be supplied into the interior of the mouth or a leak of the gargling water to be suctioned from the interior of the mouth.

In addition, according to the present disclosure, it is possible to further improve sealing performance of the tooth cleaning device by minimizing a minute spatial separation that may occur between the outer case and the connecting unit.

Further, according to the present disclosure, coupling structures of respective constituent elements are designed so that the constituent elements may be assembled in a simple manner, and it is possible to improve reliability of products by preventing the constituent elements from being easily separated.

DESCRIPTION OF DRAWINGS

FIG. 6A is an exploded perspective view of constituent elements including a first sealing unit of the hermetic tooth cleaning device according to the exemplary embodiment of the present disclosure.

FIG. 6B is a view illustrating the exploded perspective view of FIG. 6A at a different angle.

FIG. 6C is a coupled perspective view illustrating a result of assembling the constituent elements illustrated in the exploded perspective views of FIGS. 6A and 6B.

DESCRIPTION OF MAIN REFERENCE NUMERALS OF DRAWINGS

Figure 1:
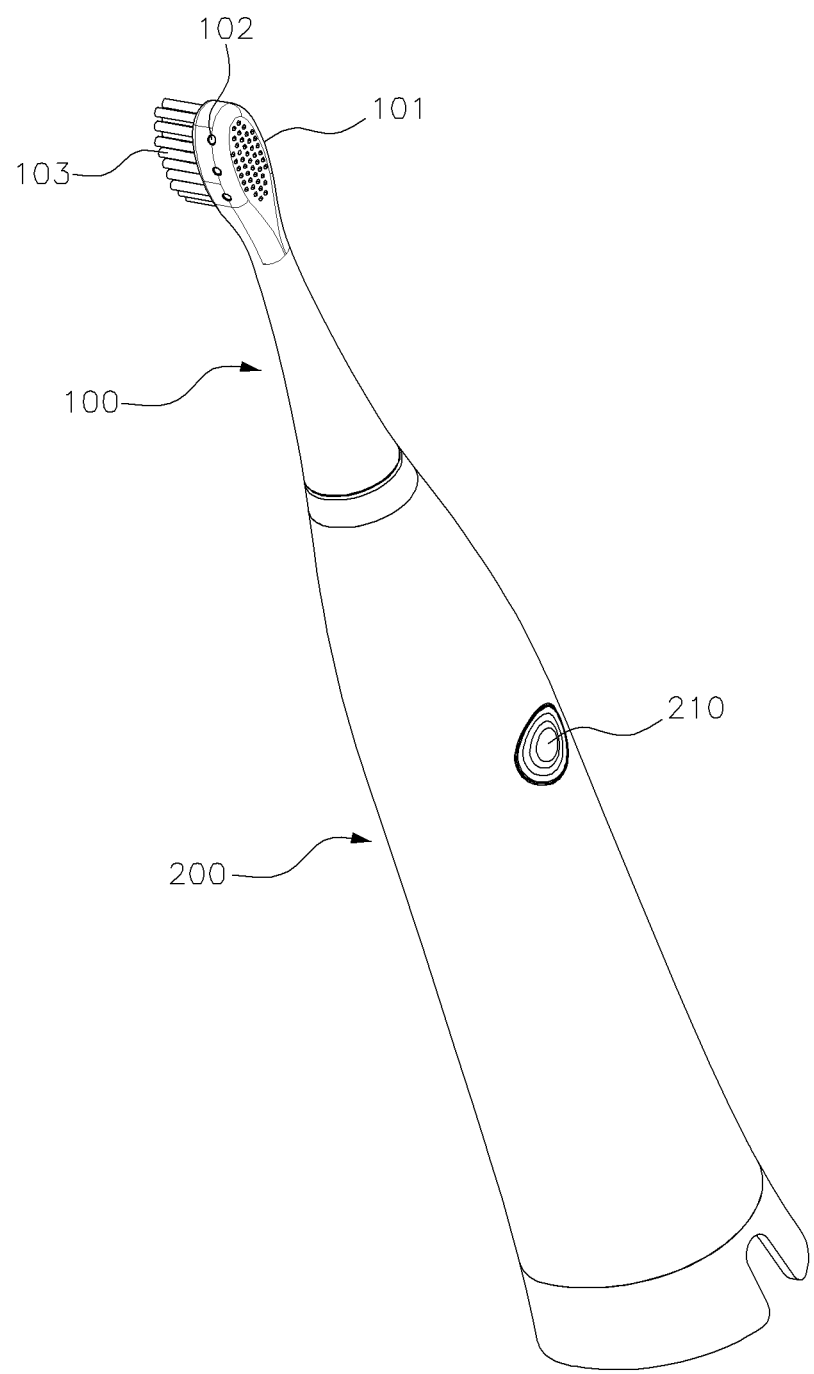
FIG. 1 is a perspective view of a hermetic tooth cleaning device according to an exemplary embodiment of the present disclosure.

10: Decorative ring
20: Screw
30: Connecting tube
100: Cleaning body
101: Cleaning head
102: Nozzle
103: Brush
104: Internal fluid conduit
105: Accommodating portion
106: The other end of accommodating portion
107: First catching projection
110: First sealing unit
111: Hollow space
112: Upper surface of first sealing unit
113: Depressed portion
120: Flange
121: Catching protrusion
122: Protruding portion
123: Coupling channel
123a: Introduction portion
123b: Extension guide portion
124: Second catching projection
125: Seating portion
200: Main body
201: Outer case
202: Groove portion
203: Coupling protruding portion
210: Operating unit
220: Connecting unit
221: Connecting flow path
222: Insertion portion
223: First fastening protruding portion 224: Second fastening protruding portion
225: Plate portion
226: Tube extension portion
230: Second sealing unit
231: Coupling recess
232: Fastening guide portion
240: Vibration motor
250: Light emitting unit
260: Power source unit
270: Drive unit
280: First bracket
290: Second bracket
300: Control unit
310: Nozzle unit
320: DC cover unit
330: DC cover guide portion
340: Bottom case

BEST MODE

Advantages and features of the present disclosure and methods of achieving the advantages and features will be clear with reference to exemplary embodiments described in detail below together with the accompanying drawings.

However, the present disclosure is not limited to exemplary embodiment disclosed herein but will be implemented in various forms. The exemplary embodiments are provided so that the present disclosure is completely disclosed, and a person of ordinary skilled in the art can fully understand the scope of the present disclosure. Therefore, the present disclosure will be defined only by the scope of the appended claims. Like reference numerals indicate like elements throughout the specification.

Hereinafter, an exemplary embodiment of the present disclosure will be described in detail with reference to the accompanying drawings.

FIG. 1 is a perspective view of a hermetic tooth cleaning device according to an exemplary embodiment of the present disclosure.

Referring to FIG. 1, the tooth cleaning device according to the exemplary embodiment of the present disclosure has a structure that broadly includes a main body 200 and a cleaning body 100.

The main body 200 includes an outer case 201 and defines a framework and an external shape of a lower portion of the tooth cleaning device, the main body 200 is a handle portion substantially grasped by a user when the user uses the tooth cleaning device, and the cleaning body 100 is a portion used to clean teeth.

The cleaning body 100 may be separably coupled to the main body 200, and a cleaning head 101 on which a brush 103 is formed in one direction may be provided at an end of the cleaning body 100. The brush 103 is used to brush the teeth, and configured such that a plurality of bristles is bundled, and the brush 103 may be separably coupled to the cleaning head 101 or formed integrally with the cleaning head 101.

The brush 103 may be coupled to the cleaning head 101 by a typical coupling method such as a threaded connection manner, or a press-fit manner, or by means of an assembling protrusion.

Nozzles 102 may be formed in an outer surface of the cleaning head 101, the nozzles 102 may be connected with a drive unit 270 that provides positive pressure or negative pressure through a flow path, and thus may spray a high-pressure washing liquid or suction gargling water in the mouth.

The nozzles 102 may be formed radially toward an outer circumferential surface of the cleaning head 101, and at least one nozzle 102 may be formed to improve efficiency in supplying the washing liquid or suctioning the gargling water in the mouth, but the shape of the nozzle 102 or the number of nozzles 102 is not limited.

An operating unit 210 may be provided on an outer circumferential surface of the main body 200, and the operating unit 210 may be a kind of a switch for operating a drive unit 270, and may perform an operation on the tooth cleaning device such as an operation of manipulating a light emitting device, and an operation of generating vibration of the toothbrush by operating a vibration motor 240.

The operating unit 210 may be formed in the form of a button, but the present disclosure is not limited thereto, and the operating unit 210 may be formed to have a structure for implementing various operating manners such as a touch manner or a sliding manner.

Figure 2:
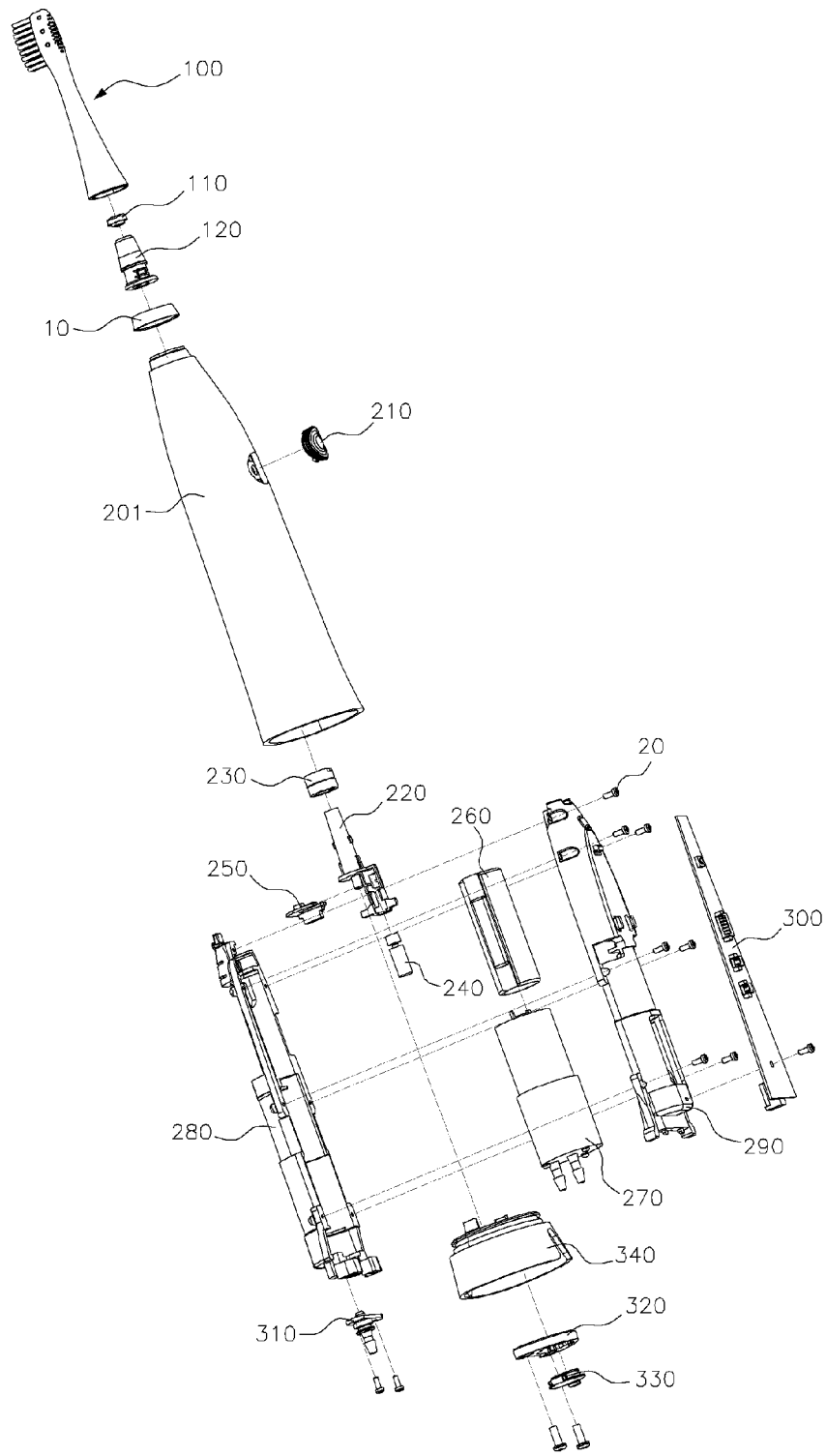
FIG. 2 is an exploded perspective view of the hermetic tooth cleaning device according to the exemplary embodiment of the present disclosure.
Figure 3:
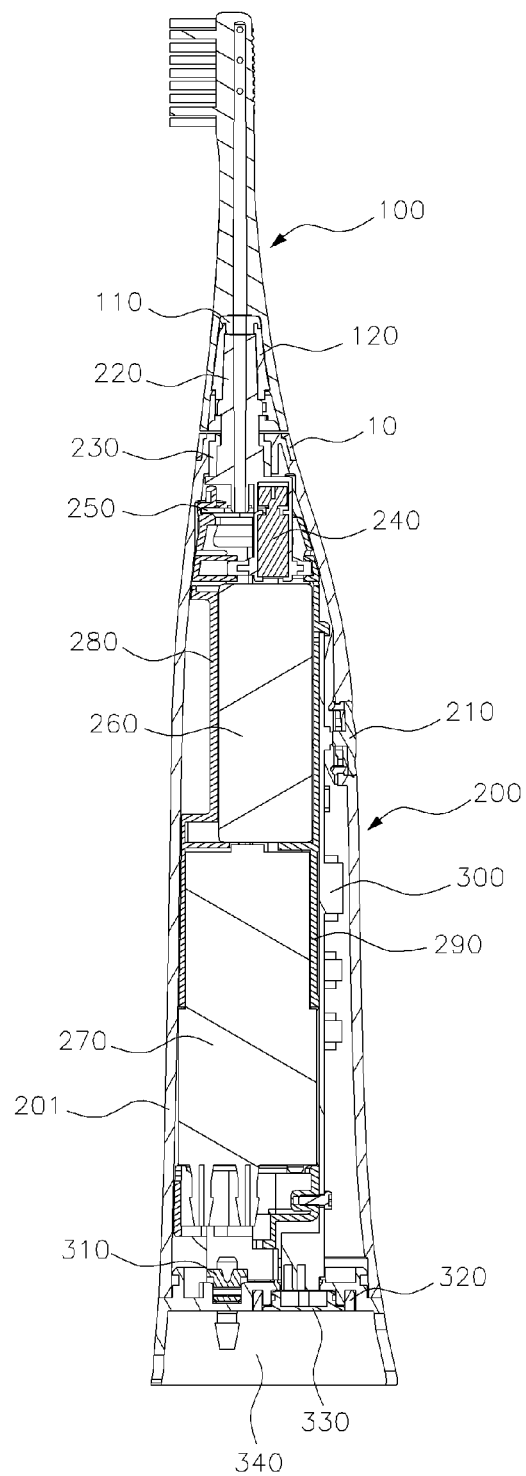
FIG. 3 is a cross-sectional view of the hermetic tooth cleaning device according to the exemplary embodiment of the present disclosure.

FIG. 2 is an exploded perspective view of the hermetic tooth cleaning device according to the exemplary embodiment of the present disclosure, and FIG. 3 is a cross-sectional view of the hermetic tooth cleaning device according to the exemplary embodiment of the present disclosure.

Referring to FIGS. 2 and 3, the hermetic tooth cleaning device according to the exemplary embodiment of the present disclosure includes the main body 200 and the cleaning body 100, and may include detailed constituent elements such as the drive unit 270 which supplies positive pressure for supplying a washing liquid or negative pressure for suctioning gargling water, a connecting unit 220 which couples the main body 200 and the cleaning body 100, a light emitting unit 250 which emits light for brightening an interior of the mouth, the vibration motor 240 which provides vibration to the cleaning body 100, a power source unit 260 which supplies electric power, a control unit 300 which is connected with the operating unit 210 and controls the drive unit 270 or the light emitting unit 250, a first bracket 280 and a second bracket 290 which fix components embedded in the main body 200, a nozzle unit 310 to which an O-ring is coupled, a DC cover unit 320 to which an O-ring is coupled, a DC cover guide portion 330 which guides the DC cover unit 320, and a bottom case 340 which is mounted at a bottom of the main body, and screws 20 which are used to assemble the brackets.

For reference, the above drawings illustrate that the detailed constituent elements such as the drive unit 270 or the power source unit 260 are provided in the cleaning body 100, but these constituent elements may of course be positioned outside the cleaning body 100 as necessary, and because basic functions or structures of the respective constituent elements are widely known, detailed descriptions thereof will be omitted.

Figure 4:
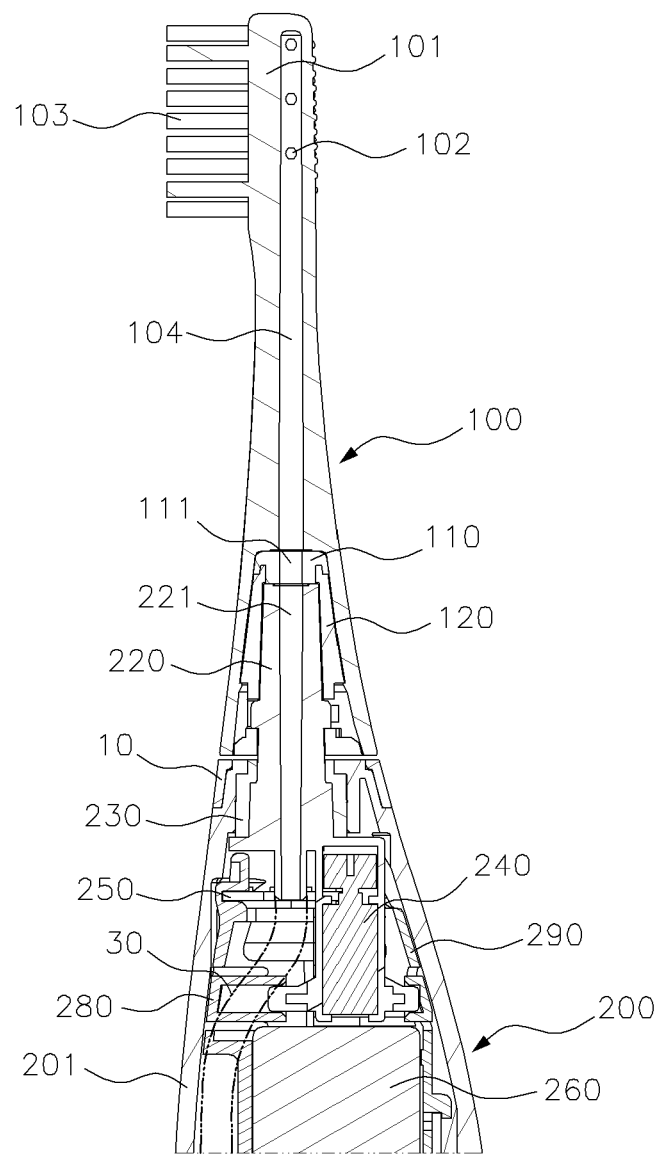
FIG. 4 is a partial cross-sectional view of the hermetic tooth cleaning device according to the exemplary embodiment of the present disclosure.

FIG. 4 is a partial cross-sectional view of the hermetic tooth cleaning device according to the exemplary embodiment of the present disclosure.

Referring to FIG. 4, the cleaning body 100 may be formed in a long bar shape, the cleaning head 101 to which the brush 103 is coupled is formed at one end of the cleaning body 100, and an internal fluid conduit 104, which extends in a longitudinal direction of the cleaning body 100 to a predetermined length, may be provided in the cleaning body 100.

The connecting unit 220 couples the main body 200 and the cleaning body 100, and has a connecting flow path 221 formed therein, one side of the connecting unit 220 may be fixedly coupled to the main body 200, and the other side of the connecting unit 220 may be inserted into an accommodating portion 105.

A first sealing unit 110, which has a hollow space 111 formed therein, may be provided between the cleaning body 100 and the connecting unit 220, and the first sealing unit 110 may prevent the occurrence of a minute spatial separation between the internal fluid conduit 104 of the cleaning body 100 and the connecting flow path 221 of the connecting unit 220, thereby improving sealing performance.

The first sealing unit 110 may be made of a material having elasticity in order to maximize sealing performance between the sub flow paths, and more particularly, the first sealing unit 110 may be made of, but not limited to, a silicone-based or rubber-based elastic body.

Figure 5:
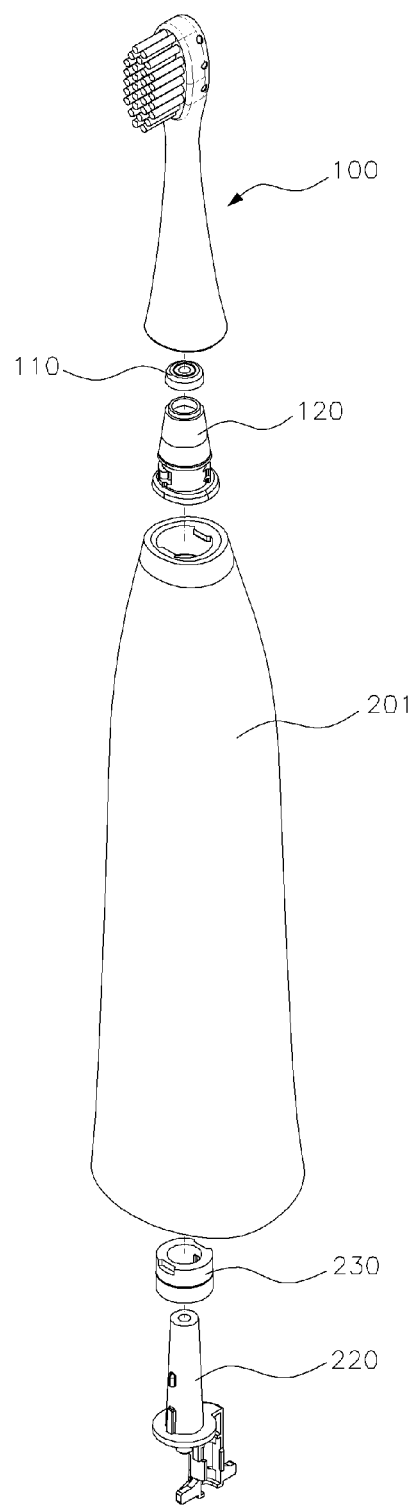
FIG. 5 is an exploded perspective view of constituent elements associated with sealing performance of the hermetic tooth cleaning device according to the exemplary embodiment of the present disclosure.

FIG. 5 is an exploded perspective view of constituent elements associated with sealing performance of the hermetic tooth cleaning device according to the exemplary embodiment of the present disclosure.

Referring to FIG. 5, the connecting unit 220 is coupled to the outer case 201 by penetrating a second sealing unit 230 in the outer case 201, the connecting unit 220, which partially protrudes to the outside of the outer case 201, is coupled to a flange 120, and the flange 120 is sequentially coupled to the first sealing unit 110 and the cleaning body 100, and coupling structures between the constituent elements will be described in detail.

FIG. 6A is an exploded perspective view of constituent elements including the first sealing unit of the hermetic tooth cleaning device according to the exemplary embodiment of the present disclosure, FIG. 6B is a view illustrating the exploded perspective view of FIG. 6A at a different angle, and FIG. 6C is a coupled perspective view illustrating a result of assembling the constituent elements illustrated in the exploded perspective views of FIGS. 6A and 6B.

Referring to FIGS. 6A to 6C, the internal fluid conduit 104 is formed in the cleaning body 100, and the accommodating portion 105, which provides a space in which the first sealing unit 110 and the flange 120 are mounted, may be formed at the other end of the cleaning body 100. The accommodating portion 105 has a structure opened at both ends thereof, one end of the accommodating portion 105 may be formed to be opened outward, and the other end of the accommodating portion 105 may be connected with the internal fluid conduit 104.

The first sealing unit 110 may be inserted into the accommodating portion 105 so that an upper surface 112 of the first sealing unit may come into contact with the other end 106 of the accommodating portion, and the flange 120 may be coupled to a lower surface of the first sealing unit 110.

The flange 120 may have a vacant hollow shape so that the connecting unit 220 may be inserted into the flange 120 and may penetrate the flange 120, and the flange 120 may be separably coupled to an outer portion of the connecting unit 220. Since the flange 120 is inserted and fixed into the accommodating portion 105, the first sealing unit 110 is pressed in a direction toward the internal fluid conduit 104 of the cleaning body 100, and as a result, it is possible to further improve sealing performance.

Meanwhile, a protruding portion 122 having a predetermined height may be formed at an end of the flange 120, and a depressed portion 113, which corresponds to the protruding portion 122, may be formed in the lower surface of the first sealing unit 110, such that as the protruding portion 122 is inserted into the depressed portion 113, the first sealing unit 110 and the flange 120 may be coupled to each other.

Specifically, the hollow space 111 is formed in the first sealing unit 110, the depressed portion 113 may be formed as an outer surface of the first sealing unit 110 is curved downward to surround an outer diameter of the hollow space 111, the protruding portion 122 may be formed at the end of the flange 120 along an outer diameter of the flange 120 so as to correspond to a height of the depressed portion 113, and the protruding portion 122 may be inserted into the depressed portion 113.

The drawings illustrate that the protruding portion 122 is formed on the flange 120 and the depressed portion 113 is formed in the first sealing unit 110, but this configuration is just an example, and the depressed portion 113 may be formed in the flange 120, and the protruding portion 122 may be formed on the first sealing unit 110.

The flange 120 may have a catching protrusion 121 formed to protrude along an outer surface of the flange 120, and a first catching projection 107, which protrudes in a center direction, may be formed on an inner surface of the accommodating portion 105, such that when the flange 120 is inserted into the accommodating portion 105, the catching protrusion 121 of the flange 120 may be caught and fixed by the first catching projection 107.

In this case, the first catching projection 107 may be formed in a curved shape in a direction in which the flange 120 is inserted, and may be formed in an orthogonal shape in a direction in which the flange 120 is withdrawn. The catching protrusion 121 of the flange 120 may be comparatively easily moved when the flange 120 is inserted into the inner surface of the accommodating portion 105, and the withdrawn of the flange 120 may be efficiently prevented after the flange 120 is inserted into the inner surface of the accommodating portion 105.

Figure 7:
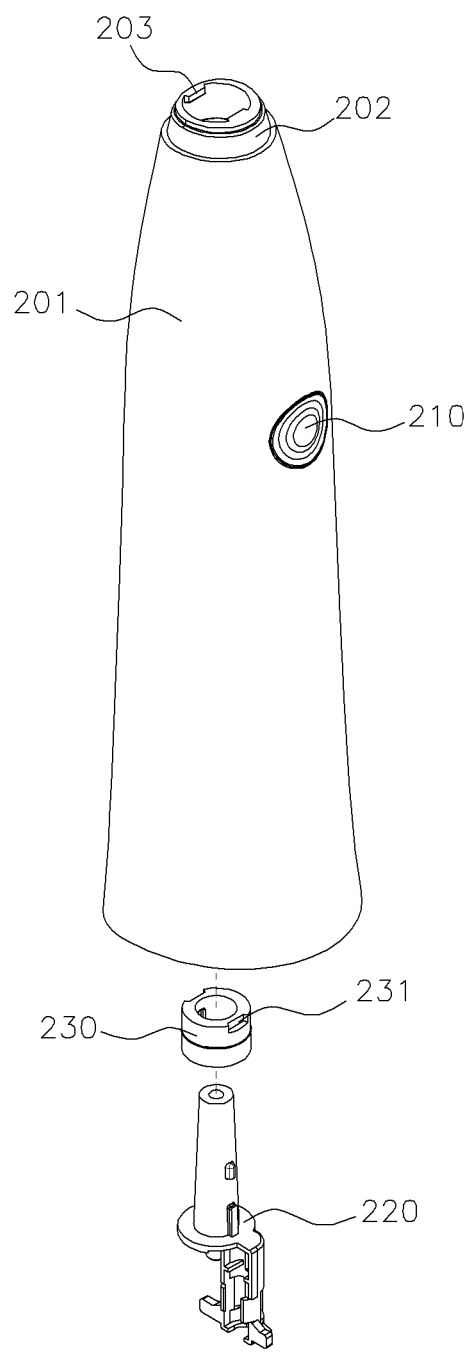
FIG. 7 is an exploded perspective view of constituent elements including a second sealing unit of the hermetic tooth cleaning device according to the exemplary embodiment of the present disclosure.
Figure 8A:
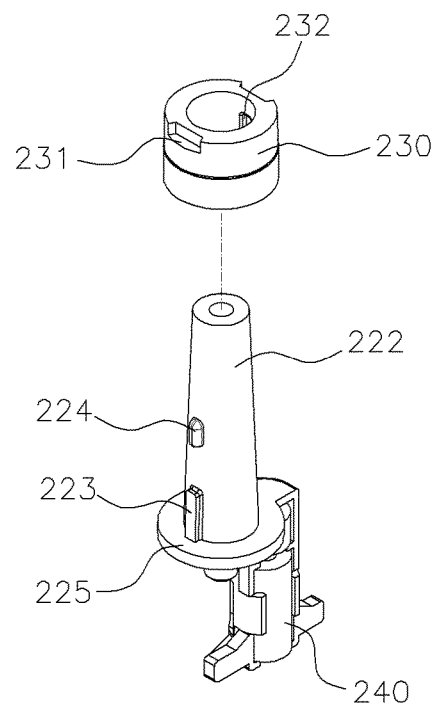
FIG. 8A is an exploded perspective view of a connecting unit and the second sealing unit according to the exemplary embodiment of the present disclosure.
Figure 8B:
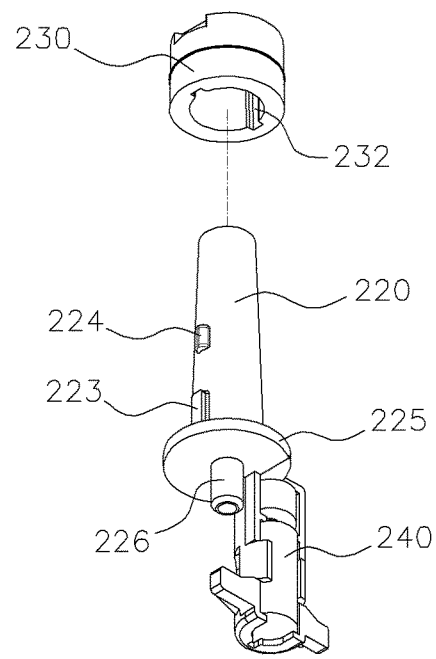
FIG. 8B is a view illustrating the exploded perspective view of FIG. 8A at a different angle.

FIG. 7 is an exploded perspective view of constituent elements including the second sealing unit of the hermetic tooth cleaning device according to the exemplary embodiment of the present disclosure, FIG. 8A is an exploded perspective view of the connecting unit and the second sealing unit according to the exemplary embodiment of the present disclosure, and FIG. 8B is a view illustrating the exploded perspective view of FIG. 8A at a different angle.

Referring to FIGS. 7, 8A, and 8B, the second sealing unit 230, which has a vacant hollow shape, may be provided between the outer case 201 and the connecting unit 220, and the connecting unit 220 may be penetratively coupled to an inner circumferential surface of the second sealing unit 230. Therefore, the second sealing unit 230 may prevent the occurrence of a minute spatial separation between the outer case 201 and the connecting unit 220, thereby further improving sealing performance.

The second sealing unit 230 may be made of a material having elasticity in order to maximize the sealing performance, and more particularly, the second sealing unit 230 may be made of, but not limited to, a silicone-based or rubber-based elastic body.

Meanwhile, the connecting unit 220 may have an insertion portion 222 which protrudes at a predetermined height so as to be inserted into the accommodating portion 105, and the second sealing unit 230 penetrates the insertion portion 222. A plate portion 225, which is formed in an approximately circular plate shape, may be formed at one end of the connecting unit 220, and a tube extension portion 226, which is positioned in the main body 200 and to which a replaceable connecting tube 30 may be coupled, may be formed on a lower surface of the plate portion 225.

First fastening protruding portions 223, which have a predetermined height and a predetermined length, may be formed on an outer surface of the insertion portion 222, fastening guide portions 232, which correspond to the first fastening protruding portions 223, may be formed in an inner surface of the second sealing unit 230, and as a result, the first fastening protruding portion 223 may be guided along the fastening guide portion 232 and then caught and fixed by an end of the fastening guide portion 232 during the process in which the insertion portion 222 is penetratively coupled to the second sealing unit 230.

The first fastening protruding portion 223 and the fastening guide portion 232 may have the same length, and in this case, the second sealing unit 230 and the plate portion 225 of the connecting unit 220 come into contact with each other in a state in which the second sealing unit 230 and the connecting unit 220 are not spaced apart from each other, and as a result, it is possible to further improve sealing performance.

The vibration motor 240 may be mounted to the connecting unit 220, and vibration generated by the vibration motor 240 may be transmitted through the connecting unit 220, and then transmitted to the cleaning body 100. That is, the connecting unit 220 may not only couple the main body 200 and the cleaning body 100, but also transmit vibration generated by the vibration motor 240 in a direction toward the cleaning body 100 as necessary by using the vibration motor 240.

Second fastening protruding portions 224 to be described below may be formed on the outer surface of the insertion portion 222, and the second fastening protruding portion 224 may be formed to be spaced upward from the first fastening protruding portion 223 at a predetermined interval, and may have a protruding height smaller than that of the first fastening protruding portion 223 so that the second fastening protruding portion 224 may pass over the fastening guide portion 232 without being caught by the fastening guide portion 232.

Coupling protruding portions 203, which protrude inward, are formed at one end of the outer case 201, and coupling recesses 231, which correspond to the coupling protruding portions 203, are formed in an upper end of the second sealing unit 230, and as a result, the coupling protruding portions 203 may be seated on the coupling recesses 231 during the process in which the connecting unit 220 is coupled to the outer case 201.

A plurality of coupling protruding portions 203 may be formed in a direction in which the plurality of coupling protruding portions 203 faces each other, and the coupling recesses 231 may be formed such that the number of coupling recesses 231 and the positions of the coupling recesses 231 correspond to those of the coupling protruding portions 203. The coupling recess 231 is formed in the upper surface of the second sealing unit 230 so as to have a predetermined size and correspond to the size of the coupling protruding portion 203, and as a result, a spatial separation between the outer case 201 and the connecting unit 220 may be minimized.

Figure 9:
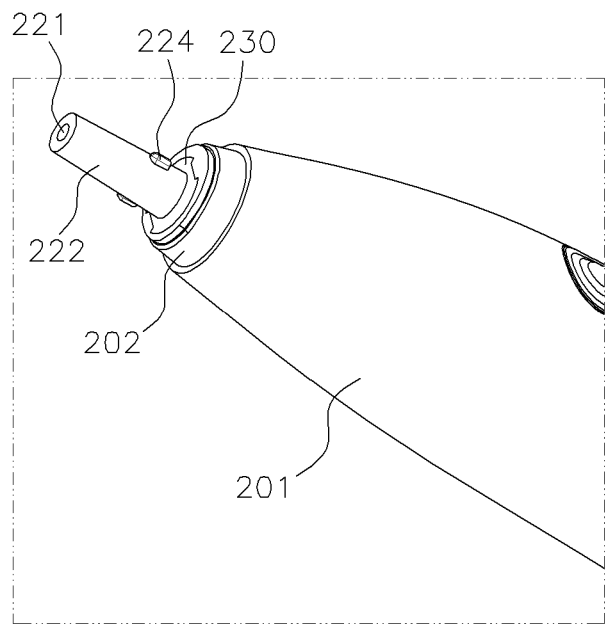
FIG. 9 is a perspective view illustrating a result of assembling the constituent elements illustrated in the exploded perspective view of FIG. 7.

FIG. 9 is a coupled perspective view illustrating a result of assembling the constituent elements illustrated in the exploded perspective view of FIG. 7.

Referring to FIG. 9, the insertion portion 222 of the connecting unit 220 protrudes to the outside of the outer case 201, the second sealing unit 230 is mounted between the outer case 201 and the connecting unit 220 so as to seal an internal space of the outer case 201, and the second fastening protruding portion 224 formed on the outer circumferential surface of the insertion portion 222 is exposed.

Figure 10:
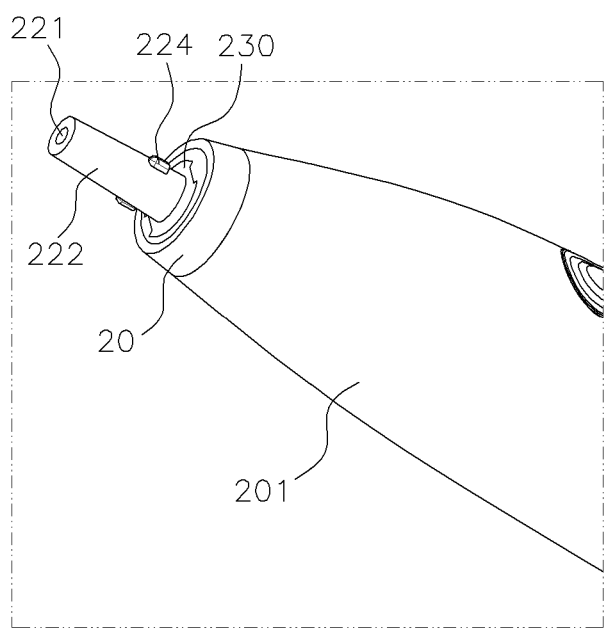
FIG. 10 is a view illustrating a result of mounting a decorative ring to the configuration in FIG. 9.

A groove portion 202 to which a decorative ring 10 is mounted may be formed at one end of the outer case 201, and FIG. 10 is a view illustrating a result of mounting a decorative ring to the configuration in FIG. 9.

Figure 11:
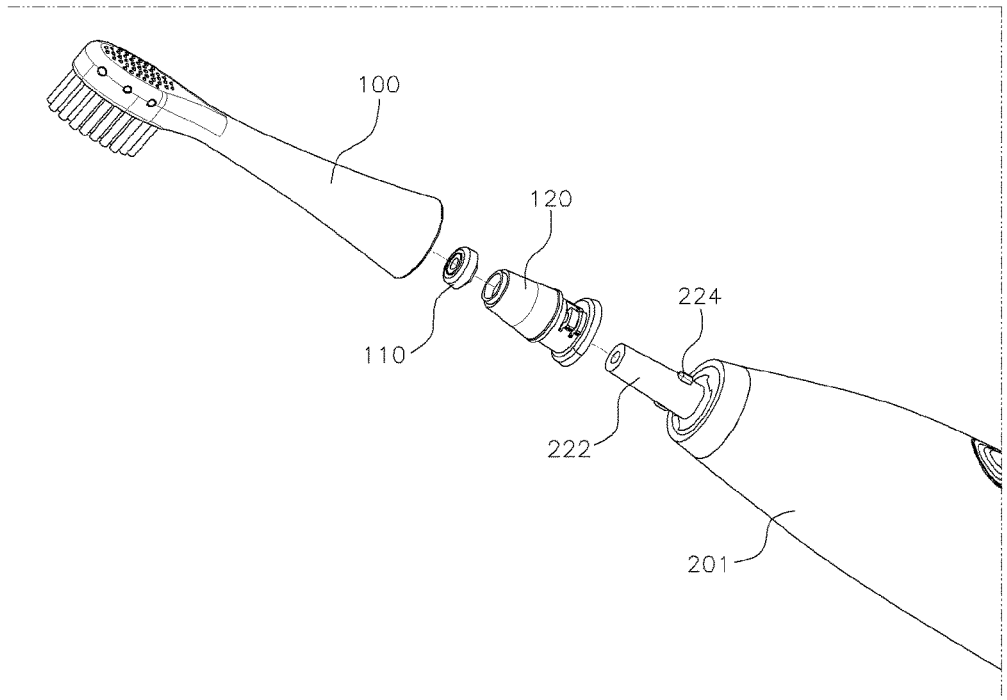
FIG. 11 is an exploded perspective view of constituent elements including the connecting unit and a cleaning body according to the exemplary embodiment of the present disclosure.
Figure 12:
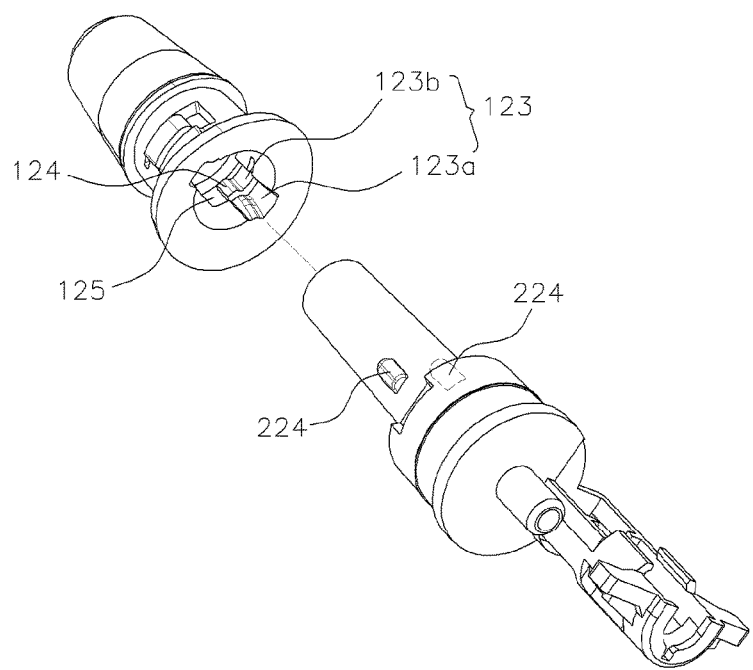
FIG. 12 is an exploded perspective view of the connecting unit and a flange according to the exemplary embodiment of the present disclosure.

FIG. 11 is an exploded perspective view of constituent elements including the connecting unit and the cleaning body according to the exemplary embodiment of the present disclosure, and FIG. 12 is an exploded perspective view of the connecting unit and the flange according to the exemplary embodiment of the present disclosure.

Referring to FIGS. 11 and 12, the second fastening protruding portions 224 are formed along the outer surface of the insertion portion 222, and coupling channels 123 are formed in the inner surface of the flange 120, and as a result, the second fastening protruding portion 224 is guided along the coupling channel 123 and then caught and fixed by one side of the coupling channel 123 during the process in which the insertion portion 222 is coupled to the flange 120, such that the connecting unit 220 and the flange 120 may be coupled to each other.

The insertion portion 222 is moved into the flange 120 so that the second fastening protruding portion 224 slides along the coupling channel 123, and the insertion portion 222 rotates after the insertion portion 222 slides to an exact position so that the second fastening protruding portion 224 is caught and fixed by one side of the coupling channel 123.

Through these processes, the internal fluid conduit 104 of the cleaning body 100, the hollow space 111 of the first sealing unit 110, and the connecting flow path 221 of the connecting unit 220 are connected to one another, thereby forming a continuous flow path.

The continuous flow path may be extended to the tube extension portion 226 of the connecting unit 220, and to the connecting tube 30 replaceably coupled to the tube extension portion 226, and the continuous flow path may be extended to a suction connecting tube or a discharge connecting tube past the drive unit 270.

Figure 13A:
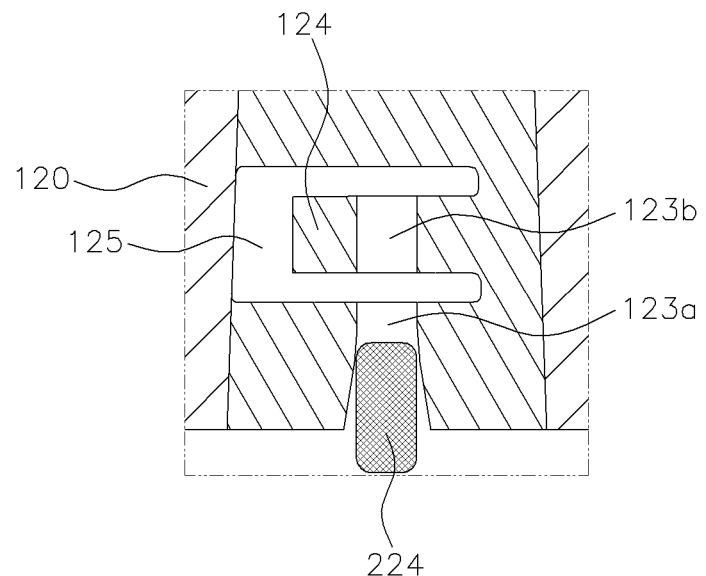
FIGS. 13A to 13C are operational state views sequentially illustrating a process of moving a second fastening protruding portion during a process of coupling an insertion portion and the flange according to the exemplary embodiment of the present disclosure.
Figure 13B:
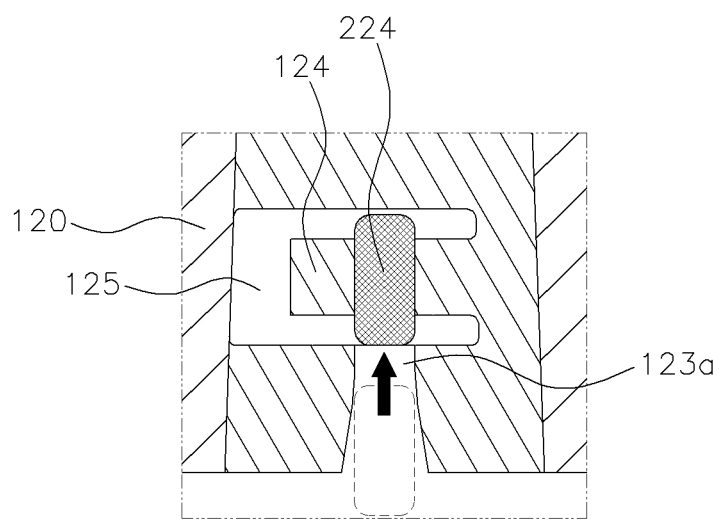
Figure 13C:
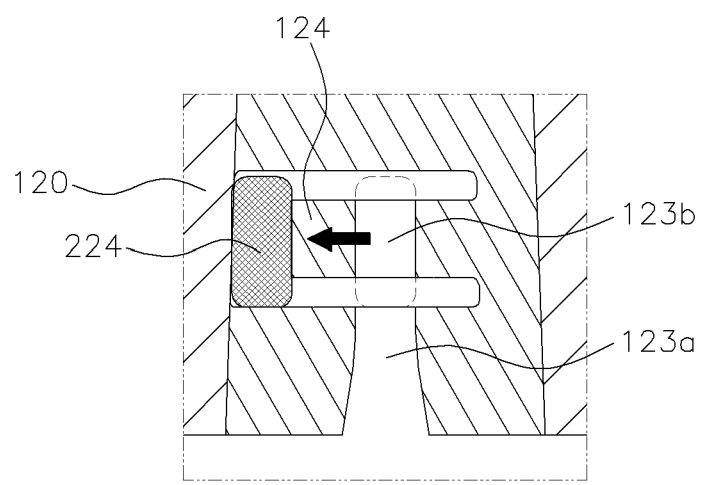

FIGS. 13A to 13C are operational state views sequentially illustrating a process of moving the second fastening protruding portion 224 during a process of coupling the insertion portion 222 and the flange 120 according to the exemplary embodiment of the present disclosure.

Referring to FIGS. 13A to 13C, the coupling channel 123 may include an introduction portion 123a which is opened outward at one end thereof, and an extension guide portion 123b which extends from the introduction portion 123a in a direction in which the flange 120 and the connecting unit 220 are coupled to each other.

To couple the flange 120 and the connecting unit 220, in a state in which the insertion portion 222 is directed toward the flange 120, the insertion portion 222 is moved first in a direction in which the connecting unit 220 and the flange 120 become close to each other. In this case, the second fastening protruding portion 224 of the connecting unit 220 is directed toward the coupling channel 123 of the flange 120, and more exactly, as illustrated in FIG. 13A, the second fastening protruding portion 224 is inserted into the flange 120 through the introduction portion 123a of the coupling channel 123.

Further, when the connecting unit 220 and the flange 120 are continuously moved in the direction in which the connecting unit 220 and the flange 120 become close to each other, the second fastening protruding portion 224 is moved along the extension guide portion 123b that extends from the introduction portion 123a in the direction in which the flange 120 and the connecting unit 220 are coupled to each other, as illustrated in FIG. 13B.

In this state, when the insertion portion 222 of the connecting unit 220 and the flange 120 are relatively rotated about a rotation axis in the longitudinal direction of the flange 120, the second fastening protruding portion 224 climbs over a second catching projection 124 formed at one side of the extension guide portion 123b of the flange 120.

Further, when the second fastening protruding portion 224 completely climbs over the second catching projection 124, the second fastening protruding portion 224 is seated on a seating portion 125 as illustrated in FIG. 13c, and as a result, the flange 120 and the connecting unit 220 may be coupled to each other, and thus it is possible to prevent the flange 120 and the connecting unit 220 from being arbitrarily rotated in the opposite direction.

In this case, the seating portion 125 may be formed by opening the flange 120 to any size along outer surfaces of the extension guide portion 123b and the second catching projection 124.

Therefore, the second catching projection 124, which is opened at three sides thereof, may be moved outward from the flange 120 to a predetermined height, and when the second fastening protruding portion 224 passes over the second catching projection 124, the second catching projection 124 is slightly pushed outward from the flange 120, thereby enabling the second fastening protruding portion 224 to be easily seated on the seating portion 125.

In this case, the second catching projection 124 may be formed to be inclined in a direction toward the extension guide portion 123b and the seating portion 125, and the second catching projection 124 may be formed such that an inclination in the direction toward the extension guide portion 123b is smaller than an inclination in the direction toward the seating portion 125 in order to allow the insertion portion 222 to be easily coupled to the flange 120 and prevent the insertion portion 222 from being easily separated.

As the foregoing, all of the constituent elements, which constitute the exemplary embodiment according to the present disclosure, have been described as being integrally coupled or operated after being coupled, but the present disclosure is not necessarily limited to the exemplary embodiment. That is, within the scope of the object of the present disclosure, one or more of all of the constituent elements can be selectively coupled and operated. In addition, unless explicitly described to the contrary, the term "comprising", "including", or "having" will be understood to imply the inclusion of stated constituent elements but not the exclusion of any other constituent elements. All terms used herein including technical or scientific terms have the same meanings as meanings which are generally understood by those skilled in the art unless they are differently defined. Terms defined in generally used dictionary shall be construed that they have meanings matching those in the context of the related art, and shall not be construed in ideal or excessively formal meanings unless they are clearly defined in the present disclosure.

The invention claimed is:

1. A hermetic tooth cleaning device comprising:
a main body which includes an outer case;
a cleaning body which is coupled to the main body, has an internal fluid conduit formed therein such that at least one nozzle is formed to be opened at one end of the internal fluid conduit, and an accommodating portion is formed at the other end of the internal fluid conduit;
a connecting unit which couples the main body and the cleaning body, has a connecting flow path formed therein, one side fixedly coupled to the main body, and the other side inserted into the accommodating portion; and
a first sealing unit which is provided between the cleaning body and the connecting unit, and has a hollow space formed therein, and prevents a spatial separation from occurring between the internal fluid conduit of the cleaning body and the connecting flow path of the connecting unit,
wherein the first sealing unit is made of an elastic body,
a flange is separably coupled to an outer portion of the connecting unit,
the flange is inserted and fixed into the accommodating portion,
a loss of positive pressure or negative pressure in a flow path is prevented, and
the flange is coupled to the outer portion of the connecting unit, which protrudes from the main body, such that the flange is disposed in the cleaning body,
wherein a second sealing unit is provided between the outer case and the connecting unit, and the connecting unit is penetratively coupled to the second sealing unit.

2. The hermetic tooth cleaning device of claim 1, wherein a protruding portion and a depressed portion, which correspond to each other, are formed at the flange and the first sealing unit, respectively, and the protruding portion is inserted into the depressed portion.

3. The hermetic tooth cleaning device of claim 1, wherein the internal fluid conduit, the hollow space, and the connecting flow path are connected to form a continuous flow path.

4. The hermetic tooth cleaning device of claim 1, wherein a first catching projection is formed on an inner surface of the accommodating portion, a catching protrusion is formed on an outer surface of the flange, and the catching protrusion is caught and fixed by the first catching projection when the flange is inserted into the accommodating portion.

5. The hermetic tooth cleaning device of claim 1, wherein the connecting unit has an insertion portion which protrudes to a predetermined height so as to be inserted into the accommodating portion.

6. The hermetic tooth cleaning device of claim 5, wherein a first fastening protruding portion and a fastening guide portion, which correspond to each other, are formed at the insertion portion and the second sealing unit, respectively, such that during a process in which the insertion portion is penetratively coupled to the second sealing unit, the first fastening protruding portion is guided along the fastening guide portion and then caught and fixed by an end of the fastening guide portion.

7. The hermetic tooth cleaning device of claim 1, wherein a coupling protruding portion, which protrudes inward, is formed at one end of the outer case, and a coupling recess, which corresponds to the coupling protruding portion, is formed at an upper end of the second sealing unit, such that during a process in which the connecting unit is coupled to the outer case, the coupling protruding portion is seated on the coupling recess.

8. The hermetic tooth cleaning device of claim 5, wherein a second fastening protruding portion and a coupling channel, which correspond to each other, are formed at the insertion portion and the flange, respectively, such that during a process in which the insertion portion is coupled to the flange, the second fastening protruding portion is guided along the coupling channel and then caught and fixed by one side of the coupling channel.

9. The hermetic tooth cleaning device of claim 8, wherein the coupling channel includes an introduction portion which is opened outward at one end thereof, and an extension guide portion which extends from the introduction portion in a direction in which the flange and the connecting unit are coupled to each other.

10. The hermetic tooth cleaning device of claim 9, wherein a second catching projection is formed at one side of the extension guide portion, and the second fastening protruding portion, which is guided to the extension guide portion, is seated on a seating portion after passing over the second catching projection.

\* \* \* \* \*